(12) United States Patent
Krimsky

(10) Patent No.: US 11,160,617 B2
(45) Date of Patent: *Nov. 2, 2021

(54) SYSTEM AND METHOD TO ACCESS LUNG TISSUE

(71) Applicant: Covidien LP, Mansfield, MA (US)

(72) Inventor: William S. Krimsky, Forest Hill, MD (US)

(73) Assignee: Covidien LP, Mansfield, MA (US)

( * ) Notice: Subject to any disclaimer, the term of this patent is extended or adjusted under 35 U.S.C. 154(b) by 74 days.

This patent is subject to a terminal disclaimer.

(21) Appl. No.: 16/683,576

(22) Filed: Nov. 14, 2019

(65) Prior Publication Data

US 2020/0078102 A1    Mar. 12, 2020

Related U.S. Application Data

(63) Continuation of application No. 15/155,830, filed on May 16, 2016, now Pat. No. 10,478,254.

(51) Int. Cl.
*A61B 34/20*    (2016.01)
*A61B 10/04*    (2006.01)
(Continued)

(52) U.S. Cl.
CPC .............. *A61B 34/20* (2016.02); *A61B 10/04* (2013.01); *A61B 1/018* (2013.01); *A61B 1/2676* (2013.01);
(Continued)

(58) Field of Classification Search
CPC ......... A61B 34/20; A61B 34/25; A61B 10/04; A61B 2090/061; A61B 2090/0811;
(Continued)

(56) References Cited

U.S. PATENT DOCUMENTS 1,576,781 A    3/1926    Phillips
1,735,726 A    11/1929    Bornhardt
(Continued)

FOREIGN PATENT DOCUMENTS

CA    964149    3/1975
DE    3042343 A1    6/1982
(Continued)

OTHER PUBLICATIONS

European Examination Report issued in corrsponding Appl. No. EP 17170976.9 dated Jan. 27, 2020 (8 pages).
(Continued)

*Primary Examiner* — Sean D Mattson
(74) *Attorney, Agent, or Firm* — Carter, DeLuca & Farrell LLP

(57) ABSTRACT

A system and method for navigating to a target site in a patient is provided. The system includes an extended working channel and a tool usable with an electromagnetic navigation system. In particular, the extended working channel and the tool contain an electromagnetic sensor configured to provide location information within a patient of the extended working channel and the tool to the electromagnetic navigation system. The distance from the tool and the target site can then be determined and displayed to a clinician on a display device.

20 Claims, 8 Drawing Sheets

(51) Int. Cl.
*A61B 90/00* (2016.01)
*A61B 5/00* (2006.01)
*A61B 18/00* (2006.01)
*A61B 18/14* (2006.01)
*A61B 34/00* (2016.01)
*A61B 5/06* (2006.01)
*A61B 1/018* (2006.01)
*A61B 34/10* (2016.01)
*A61B 1/267* (2006.01)

(52) U.S. Cl.
CPC ............ *A61B 5/062* (2013.01); *A61B 5/6852* (2013.01); *A61B 18/1492* (2013.01); *A61B 34/25* (2016.02); *A61B 90/39* (2016.02); *A61B 2018/00541* (2013.01); *A61B 2034/107* (2016.02); *A61B 2034/2051* (2016.02); *A61B 2034/2065* (2016.02); *A61B 2034/2068* (2016.02); *A61B 2090/061* (2016.02); *A61B 2090/0811* (2016.02)

(58) Field of Classification Search
CPC ............... A61B 5/6852; A61B 5/062; A61B 2018/00541; A61B 90/39; A61B 18/1492; A61B 1/018; A61B 1/2676; A61B 2034/107; A61B 2034/2051; A61B 2034/2065; A61B 2034/2068
See application file for complete search history.

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | DeCant, Jr. et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,769,005 A | 9/1988 | Ginsburg et al. |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |

(56) References Cited

U.S. PATENT DOCUMENTS

| | | |
|---|---|---|
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,403,321 A | 4/1995 | DiMarco |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |

(56) References Cited

U.S. PATENT DOCUMENTS

| | | |
|---|---|---|
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |

(56) References Cited

U.S. PATENT DOCUMENTS

| | | |
|---|---|---|
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,964,793 A | 10/1999 | Rutten et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,112,111 A | 8/2000 | Glantz |
| 6,118,845 A | 9/2000 | Simon et al. |
| 6,122,538 A | 9/2000 | Sliwa, Jr. et al. |
| 6,122,541 A | 9/2000 | Cosman et al. |
| 6,129,698 A | 10/2000 | Beck |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,192,280 B1 | 2/2001 | Sommer et al. |
| 6,194,639 B1 | 2/2001 | Botella et al. |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,211,666 B1 | 4/2001 | Acker |
| 6,213,995 B1 | 4/2001 | Steen et al. |
| 6,216,026 B1 | 4/2001 | Kuhn et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,304,769 B1 | 10/2001 | Arenson et al. |
| 6,314,310 B1 | 11/2001 | Ben-Haim et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,351,659 B1 | 2/2002 | Vilsmeier |
| 6,366,799 B1 | 4/2002 | Acker et al. |
| 6,373,240 B1 | 4/2002 | Govari |
| 6,381,485 B1 | 4/2002 | Hunter et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,534,982 B1 | 3/2003 | Jakab |
| 6,551,325 B2 | 4/2003 | Neubauer et al. |
| 6,580,938 B1 | 6/2003 | Acker |
| 6,584,174 B2 | 6/2003 | Schubert et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,618,612 B1 | 9/2003 | Acker et al. |
| 6,628,980 B2 | 9/2003 | Atalar et al. |
| 6,640,128 B2 | 10/2003 | Vilsmeier et al. |
| 6,650,927 B1 | 11/2003 | Keidar |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,711,429 B1 | 3/2004 | Gilboa et al. |
| 6,788,967 B2 | 9/2004 | Ben-Haim et al. |
| 6,834,201 B2 | 12/2004 | Gillies et al. |
| 6,995,729 B2 | 2/2006 | Govari et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,248,914 B2 | 7/2007 | Hastings et al. |
| 7,286,868 B2 | 10/2007 | Govari |
| 7,301,332 B2 | 11/2007 | Govari et al. |
| 7,321,228 B2 | 1/2008 | Govari |

(56) References Cited

U.S. PATENT DOCUMENTS

| | | |
|---|---|---|
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,720,521 B2 | 5/2010 | Chang et al. |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,809,421 B1 | 10/2010 | Govari |
| 8,206,380 B2 | 6/2012 | Lenihan et al. |
| 8,611,984 B2 | 12/2013 | Greenburg et al. |
| 8,731,684 B2 | 5/2014 | Carr et al. |
| 8,926,605 B2 | 1/2015 | McCarthy et al. |
| 8,954,161 B2 | 2/2015 | McCarthy et al. |
| 8,961,506 B2 | 2/2015 | McCarthy et al. |
| 9,113,813 B2 | 8/2015 | Greenburg et al. |
| 9,121,774 B2 | 9/2015 | Brannan |
| 10,478,254 B2 * | 11/2019 | Krimsky ............... A61B 10/04 |
| 2001/0007918 A1 | 7/2001 | Vilsmeier et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2002/0062203 A1 | 5/2002 | Gilboa |
| 2002/0095081 A1 | 7/2002 | Vilsmeier |
| 2002/0128565 A1 | 9/2002 | Rudy |
| 2002/0173689 A1 | 11/2002 | Kaplan |
| 2002/0193686 A1 | 12/2002 | Gilboa |
| 2003/0018251 A1 | 1/2003 | Solomon |
| 2003/0074011 A1 | 4/2003 | Gilboa et al. |
| 2003/0086599 A1 | 5/2003 | Armato et al. |
| 2003/0142753 A1 | 7/2003 | Gunday |
| 2003/0160721 A1 | 8/2003 | Gilboa et al. |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2005/0033149 A1 | 2/2005 | Strommer et al. |
| 2005/0085715 A1 | 4/2005 | Dukesherer et al. |
| 2005/0107688 A1 | 5/2005 | Strommer |
| 2005/0119527 A1 | 6/2005 | Banik et al. |
| 2005/0197566 A1 | 9/2005 | Strommer et al. |
| 2006/0015126 A1 | 1/2006 | Sher |
| 2006/0052689 A1 * | 3/2006 | Scouten ............... A61B 34/20 600/417 |
| 2006/0058647 A1 | 3/2006 | Strommer et al. |
| 2006/0064006 A1 | 3/2006 | Strommer et al. |
| 2006/0149134 A1 | 7/2006 | Soper et al. |
| 2006/0184016 A1 * | 8/2006 | Glossop ............... A61B 1/2676 600/434 |
| 2007/0135803 A1 | 6/2007 | Belson |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0265639 A1 | 11/2007 | Danek et al. |
| 2007/0287901 A1 | 12/2007 | Strommer et al. |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2008/0262473 A1 | 10/2008 | Kornblau |
| 2009/0182224 A1 | 7/2009 | Shmarak et al. |
| 2009/0292166 A1 * | 11/2009 | Ito ..................... A61B 1/00009 600/109 |
| 2011/0230758 A1 | 9/2011 | Eichler |
| 2012/0035603 A1 | 2/2012 | Lenihan |
| 2012/0289776 A1 | 11/2012 | Keast et al. |
| 2014/0051987 A1 | 2/2014 | Kowshik et al. |
| 2015/0105765 A1 | 4/2015 | Panescu et al. |
| 2016/0000303 A1 | 1/2016 | Klein et al. |
| 2016/0000517 A1 | 1/2016 | Kehat et al. |
| 2016/0051221 A1 | 2/2016 | Dickhans et al. |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 41213426 A1 | 10/1992 |
| DE | 4225112 C1 | 12/1993 |
| DE | 4233978 C1 | 4/1994 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0651968 A1 | 5/1995 |
| EP | 0655138 B1 | 5/1995 |

(56) References Cited

FOREIGN PATENT DOCUMENTS

| | | |
|---|---|---|
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1374793 A1 | 1/2004 |
| EP | 2096523 A1 | 9/2009 |
| EP | 2123216 A1 | 11/2009 |
| EP | 2238901 A2 | 10/2010 |
| EP | 2364660 A1 | 9/2011 |
| EP | 2377457 A1 | 10/2011 |
| FR | 2417970 A1 | 9/1979 |
| FR | 2618211 A1 | 1/1989 |
| GB | 2094590 A | 9/1982 |
| GB | 2164856 A | 4/1986 |
| JP | 63240851 A | 10/1988 |
| JP | 03267054 A | 11/1991 |
| JP | 06194639 A | 7/1994 |
| WO | 8809151 A1 | 12/1988 |
| WO | 8905123 A1 | 6/1989 |
| WO | 9005494 A1 | 5/1990 |
| WO | 9103982 A1 | 4/1991 |
| WO | 9104711 A1 | 4/1991 |
| WO | 9107726 A1 | 5/1991 |
| WO | 9203090 A1 | 3/1992 |
| WO | 9206645 A1 | 4/1992 |
| WO | 9404938 A1 | 3/1994 |
| WO | 9423647 A1 | 10/1994 |
| WO | 9424933 A1 | 11/1994 |
| WO | 9507055 A1 | 3/1995 |
| WO | 9605768 A1 | 2/1996 |
| WO | 9611624 A2 | 4/1996 |
| WO | 9632059 A1 | 10/1996 |
| WO | 9700043 A1 | 1/1997 |
| WO | 97/29684 A1 | 8/1997 |
| WO | 9736192 A1 | 10/1997 |
| WO | 9749453 A1 | 12/1997 |
| WO | 9808554 A1 | 3/1998 |
| WO | 9839808 A1 | 9/1998 |
| WO | 9915097 A2 | 4/1999 |
| WO | 9918852 A1 | 4/1999 |
| WO | 9921498 A1 | 5/1999 |
| WO | 9923956 A1 | 5/1999 |
| WO | 9926549 A1 | 6/1999 |
| WO | 9927839 A2 | 6/1999 |
| WO | 9929253 A1 | 6/1999 |
| WO | 9933406 A1 | 7/1999 |
| WO | 9937208 A1 | 7/1999 |
| WO | 9938449 A1 | 8/1999 |
| WO | 9952094 A1 | 10/1999 |
| WO | 9960939 A1 | 12/1999 |
| WO | 0006701 A1 | 2/2000 |
| WO | 0010456 A1 | 3/2000 |
| WO | 0035531 A1 | 6/2000 |
| WO | 0130437 A1 | 5/2001 |
| WO | 0187136 A2 | 11/2001 |
| WO | 02064011 A2 | 8/2002 |
| WO | 02/070047 A1 | 9/2002 |
| WO | 03086498 A2 | 10/2003 |
| WO | 2004/023986 A1 | 3/2004 |
| WO | 2005115235 A1 | 12/2005 |
| WO | 2006116597 A2 | 11/2006 |
| WO | 2008002517 A1 | 1/2008 |
| WO | 2008042423 A2 | 4/2008 |
| WO | 2009/150563 A2 | 12/2009 |
| WO | 2011/104664 A1 | 9/2011 |
| WO | 2013158392 A2 | 10/2013 |
| WO | 2014025550 A1 | 2/2014 |
| WO | 2015023665 A1 | 2/2015 |
| WO | 2016033066 A1 | 3/2016 |
| WO | 2016/183226 | 11/2016 |

OTHER PUBLICATIONS

Extended European Search Report issued in Application No. EP 17170976.9 dated Sep. 8, 2017 (13 pages).
Australian Examination Report issued in Appl. No. AU 2017202738 dated Feb. 5, 2018 (3 pages).
Canadian Office Action issued in Appl. No. CA 2,967,198 dated May 24, 2018 (3 pages).
Australian Examination Report No. 2 issued in Appl. No. AU 2017202738 dated Jun. 25, 2018.

* cited by examiner

SYSTEM AND METHOD TO ACCESS LUNG TISSUE

CROSS-REFERENCE TO RELATED APPLICATIONS

This application is a continuation application of U.S. patent application Ser. No. 15/155,830, filed on May 16, 2016, the entire contents of which are incorporated herein by reference.

BACKGROUND

The present disclosure relates generally to systems and methods for navigating a tool, such as a catheter, probe, or medical device, through a luminal network of a patient's body to a target site and tracking the location of the tool relative to the target site.

A common device for inspecting and navigating the airway of a patient is a bronchoscope. Typically, the bronchoscope is inserted into a patient's airways through the patient's nose or mouth and can extend into the lungs of the patient. In navigating to a region of interest, bronchoscopes, however, are limited in how far they may be advanced through the airways due to their size. In instances in which the bronchoscope is too large to be located at a region of interest deep in the lungs, a clinician may advance smaller diameter catheters and/or tools through the bronchoscope to reach the location. To aid in the navigation of the catheter and/or tool through the bronchoscope, the clinician may utilize real-time imaging modalities such as computerized tomographic (CT) images. These images enable the development of three-dimensional models of the airways or other luminal networks, typically from a series of computed tomography (CT) images. While the system described above is quite capable, improvements may be made.

SUMMARY

Provided in accordance with the present disclosure is a method of navigating a tool to a target site. The method includes first identifying a location of a target site within a patient's body. The location of a tool having a first sensor disposed on the tool is then tracked and a distance between the location of the target site and the tracked location of the tool first sensor is determined. The tracking of the location of the first sensor may include receiving orientation data corresponding to the first sensor. In an embodiment, the tool is a needle, a guide wire, a biopsy tool, a dilator, or an ablation device. The determined distance between the location of the target site and the tool is then displayed. The identification of a location of a target site within a patient's body may include obtaining a plurality of images of the patient's body and then identifying the location of the target site from the plurality of images, the plurality of images may be stored images. The plurality of images may also include computer tomography (CT) images, ultrasound images, magnetic resonance images (MRI), fluoroscopic images, or endoscopic images. Additionally, the location of the target site may be identified by displaying images of the patient's body and receiving an input on one or more of the images indicating the location of the target site. In one embodiment, the target site may include a biomarker or other localization materials, which can be used to identify the location of the target site and sensed by the first sensor.

In one embodiment, the method further includes detecting a change in location of the first sensor on the tool and determining a distance between the location of the target site and the change in location of the first sensor. The displayed distance between the location of the target site and the first sensor is then updated. The method may further include the tracking of a location of a second sensor on a catheter configured to receive the tool and determining a distance between the location of the first sensor and the second sensor. The distance between the location of the first sensor and the second sensor is then displayed. The catheter may be an extended working channel (EWC), a needle, a guide wire, a biopsy tool, a dilator, or an ablation device.

Also provided in accordance with the present disclosure is a navigation system including a tool configured to be advanced through a patient's luminal network, the tool having a first sensor, a display configured to display an image of a portion of the patient's luminal network, a controller coupled to the display, and a memory. The memory stores instructions that when executed by the controller cause the controller to identify a location of a target site within a patient's body, track a location of the tool having the first sensor, determine a distance between the location of the target site and the tool, and display, on the display, the distance between the location of the target site and the tool. The tool may be an extended working channel (EWC), a needle, a guide wire, a biopsy tool, a dilator, or an ablation device. The navigation system may further comprise a catheter configured to receive the tool, the catheter having a second sensor. In an embodiment, the first sensor and/or the second sensor may be an electromagnetic sensor. In an embodiment, the memory further causes the controller to track a location of the catheter having the second sensor, determine a distance between the location of the tool and the catheter, and display, on the display, the distance between the location of the tool and the catheter.

In an embodiment, the tool is lockable relative to the catheter. The tool can be locked to the catheter with a clip, luer lock, or a thread. In another embodiment, the tool includes a hub wherein the first sensor is disposed circumferentially around the hub.

BRIEF DESCRIPTION OF THE DRAWINGS

Various embodiments of the present disclosure are described herein with reference to the drawings wherein.

DETAILED DESCRIPTION

The present disclosure is directed to a navigation system and a method for determining and displaying the distance between a tool and a target site. Generally, a sensor is included on the tool to thereby permit the sensing and tracking of the tool's location. Using the location of the tool, the system calculates a distance between the tool and the target site, and displays the distance to a user. The system may detect movement of the sensor, causing the distance between the tracked tool and the target site to be recalculated and the display to be updated with the recalculated distance.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
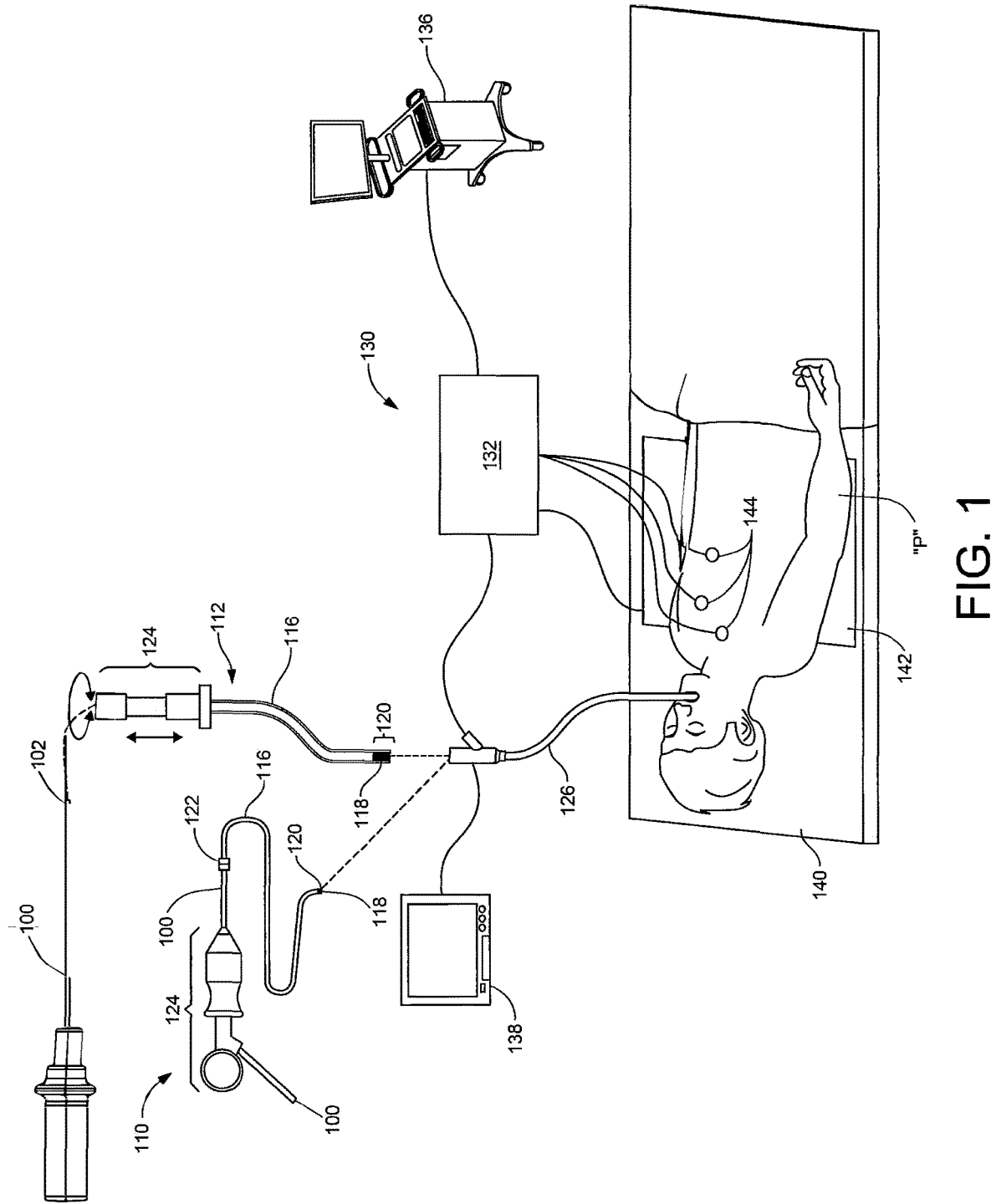
FIG. 1 is a schematic illustration of an electromagnetic navigation (EMN) system and two catheter guide assemblies configured to be used with the EMN system, in accordance with an embodiment of the present disclosure.

FIG. 1 shows an electromagnetic navigation (EMN) system 130 configured for use with a catheter guide assembly 110, 112, in accordance with an illustrative embodiment of the present disclosure. The EMN system 130 is configured to utilize computerized tomography (CT) imaging, magnetic resonance imaging (MRI), ultrasonic imaging, endoscopic imaging, fluoroscopic imaging, or another modality to create a roadmap of a patient's lungs. One such EMN system 130 is the ELECTROMAGNETIC NAVIGATION BRONCHOSCOPY® system currently sold by Medtronic Inc. The EMN system 130 generally includes a bronchoscope 126 configured to receive one or more types of catheter guide assemblies 110, 112, monitoring equipment 138, an electromagnetic field generator 142, a tracking module 132, and a workstation 136. FIG. 1 also depicts a patient "P" lying on an operating table 140 including an electromagnetic field generator 142. The positions of a number of reference sensors 144 placed on the patient "P" in the magnetic field generated by the electromagnetic field generator 142 can be determined by the tracking module 132. The EMN system 130 uses the reference sensors 144 to calculate a patient coordinate frame of reference.

Each of the catheter guide assemblies 110, 112 includes a control handle 124 and an extended working channel (EWC) 116 that is configured to receive a tool 100. The EWC 116 includes an electromagnetic (EM) sensor 120 located on a distal end 118 of the EWC 116. The tool 100 may be any one of a variety of medical devices including, but not limited to, a needle, a guide wire, a biopsy tool, a dilator, or an ablation device. In an embodiment, the tool 100 also includes an EM sensor 102. The EM sensors 102, 120 work in conjunction with the tracking module 132 to enable tracking and navigation of the EM sensors 102, 120 within the magnetic field generated by the electromagnetic field generator 142. In particular, the tracking module 132 enables navigation and tracking of the EM sensors 102, 120, including receiving orientation data corresponding to the EM sensors 102, 120, within a luminal network of a patient "P" to arrive at a target site. EM sensors 102, 120 may be any number of types of location sensors, including ring sensors, optical sensors, radiofrequency sensors, ferromagnetic sensors, hollow sensors, and the like. In an embodiment where EM sensor 120 is a hollow sensor, the hollow sensor can be configured to measure a distance that the tool 100 advances past the distal end 118 of the EWC 116.

Figure 2:
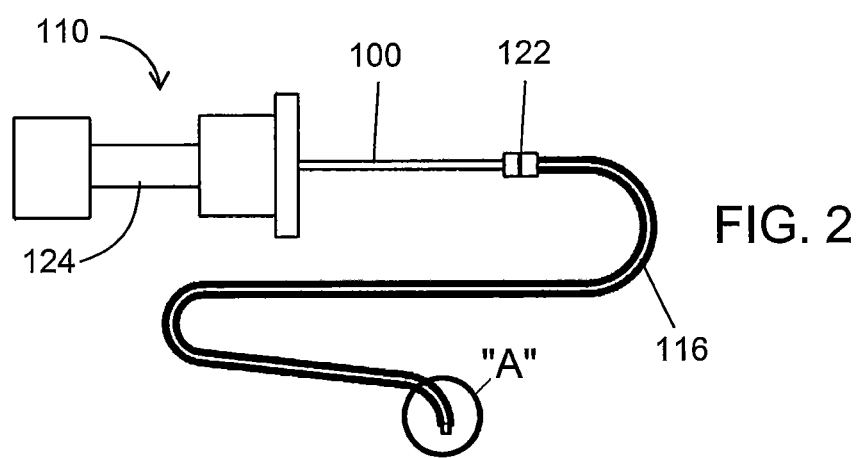
FIG. 2 is a perspective view of a catheter guide assembly of the EMN system of FIG. 1, in accordance with the present disclosure.

With additional reference to FIG. 2, a catheter guide assembly 110 is shown, in accordance with an embodiment of the present disclosure. In addition to including the EWC 116 and tool 100, the catheter guide assembly 110 includes a control handle 124, which enables advancement and steering of the distal end of the catheter guide assembly 110. Once inserted in the EWC 116, the tool 100 can be locked to the EWC 116 with a locking mechanism 122. The locking of tool 100 to the EWC 116 allows the tool 100 and the EWC 116 to travel together through a luminal network of the patient "P." The locking mechanism 122 may be a simple clip or luer lock, or the tool 100 may have a threaded configuration that allows it to threadably engage with and lock to the EWC 116. Examples of catheter guide assemblies usable with the instant disclosure are currently marketed and sold by Medtronic Inc. under the name SUPERDIMENSION® Procedure Kits and EDGE™ Procedure Kits. For a more detailed description of the catheter guide assemblies, reference is made to commonly-owned U.S. Patent Application Publication Number 2014/0046315 filed on Mar. 15, 2013, by Ladtkow et al. and U.S. Pat. No. 7,233,820, the entire contents of which are incorporated in this disclosure by reference.

Figure 2A:
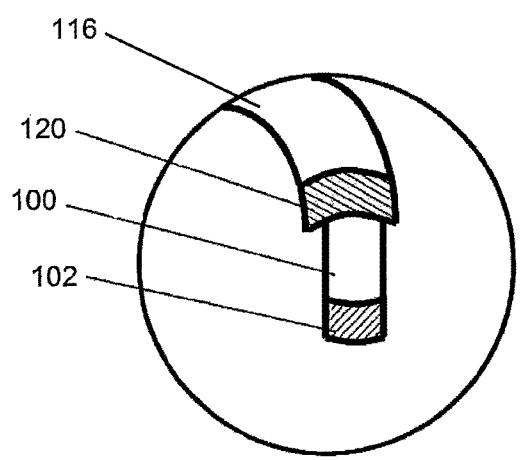
FIG. 2A is an enlarged view of an embodiment of a distal portion of the catheter guide assembly of FIG. 2 indicated by area "A"
Figure 2B:
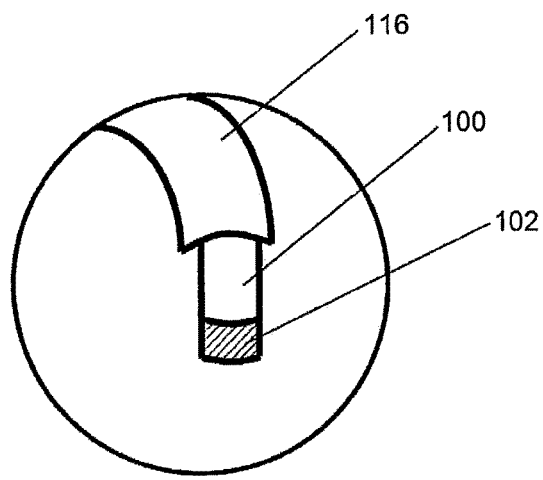
FIG. 2B is an enlarged view of an alternative embodiment of the distal portion of the catheter guide assembly of FIG. 2 indicated by area "A"
Figure 2C:
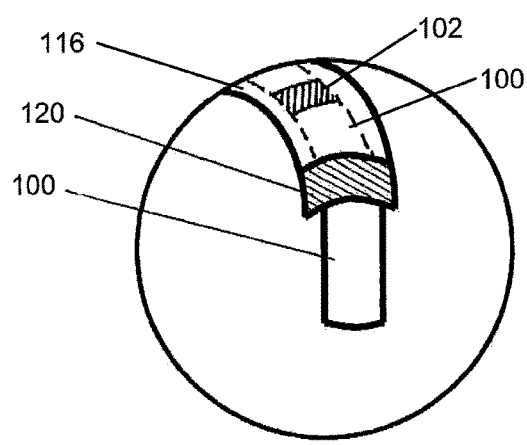
FIG. 2C is an enlarged view of another alternative embodiment of the distal portion of the catheter guide assembly of FIG. 2 indicated by area "A"

FIG. 2A is an enlarged view of a distal end of the catheter assembly 110 indicated by an encircled area "A" in FIG. 2. Here, the EWC 116 including an EM sensor 120 is shown receiving a tool 100, which on its distal end includes an EM sensor 102. FIG. 2B depicts a different embodiment of the distal end of the catheter assembly 110 except that in this embodiment, the EWC 116 does not include an EM sensor. FIG. 2C depicts yet another embodiment of the catheter assembly 110 in which the EM sensor 102 is disposed at a location that is closer to a proximal end of the tool 100. No matter the particular configuration, the EM sensors 102, 120 on the distal portion of the EWC 116 and/or the tool 100 are sensed by the electromagnetic field produced by the electromagnetic generator, and are used to identify the location of the EWC 116 and/or the tool 100 in the electromagnetic field. The EM sensors 102, 120 are used to navigate the EWC 116 and/or tool 100 through a luminal network of the patient "P." In this particular embodiment, the luminal network is the patient's lung.

Figure 3:
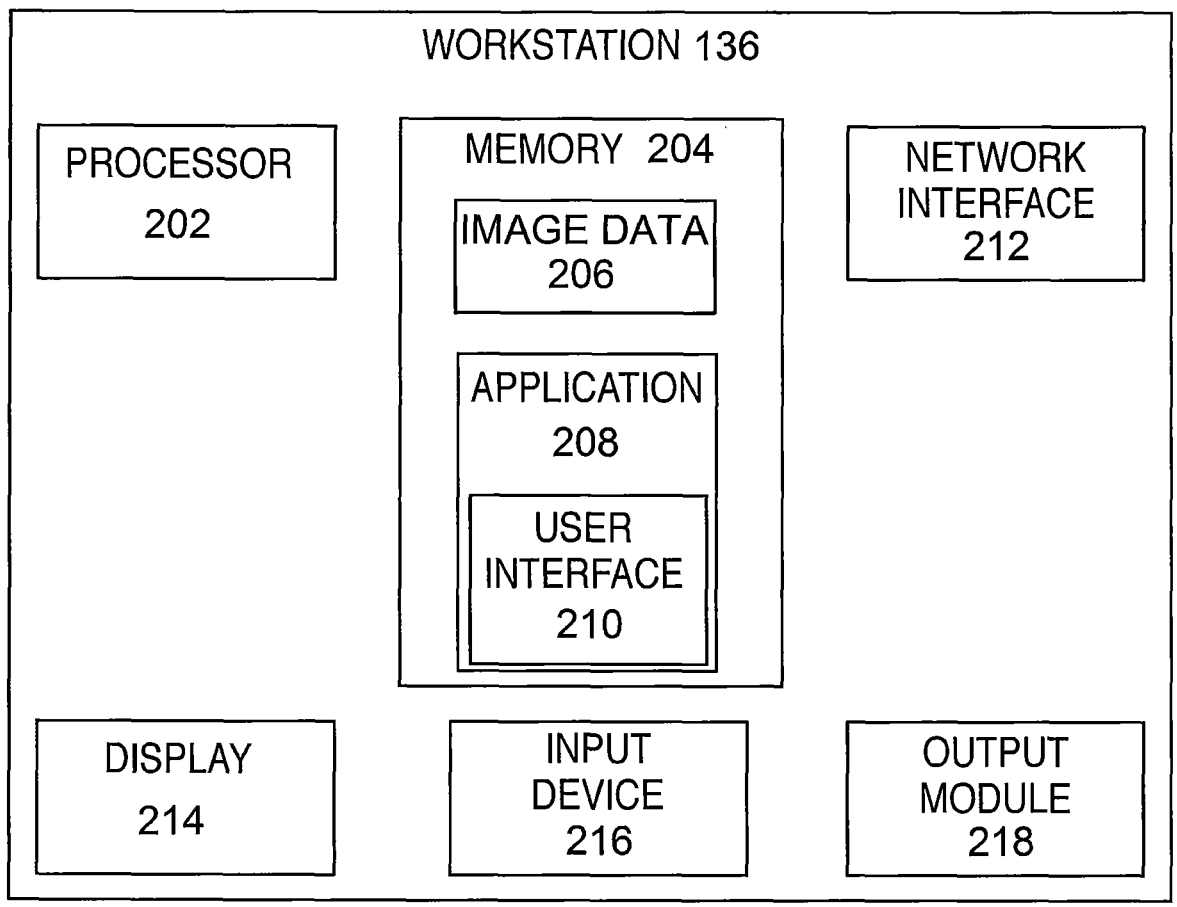
FIG. 3 is a schematic of the components of a workstation that may be implemented in the EMN system of FIG. 1, in accordance with an embodiment of the present disclosure.

As noted briefly above, the tracking module 132 receives data received from the EM sensors 102, 120 and provides the data to the workstation 136 for use in planning and navigation. Turning now to FIG. 3, in order to operate as described, workstation 136 may include memory 204, processor 202, display 214, network interface 212, input device 216, and/or output module 218. Memory 204 includes any non-transitory computer-readable storage media for storing data and/or software that is executable by processor 202 and which controls the operation of workstation 136. In an embodiment, memory 204 may include one or more solid-state storage devices such as flash memory chips. Alternatively or in addition to the one or more solid-state storage devices, memory 204 may include one or more mass storage devices connected to the processor 202 through a mass storage controller (not shown) and a communications bus (not shown).

Memory 204 may store application 208 and/or image data 206. Application 208 may, when executed by processor 202 cause a display associated with workstation 136 to present user interface 210. Network interface 212 may be configured to connect to a network such as a local area network (LAN) consisting of a wired network and/or a wireless network, a wide area network (WAN), a wireless mobile network, a Bluetooth network, and/or the internet. Input device 216 may be any device by means of which a user may interact with workstation 136, such as, for example, a mouse, keyboard, foot pedal, touch screen, and/or voice interface. Output module 218 may include any connectivity port or bus, such as, for example, parallel ports, serial ports, universal serial busses (USB), or any other similar connectivity port known to those skilled in the art.

Prior to the start of navigation, a clinician loads a navigation plan into application 208 from memory 204, a USB device, or from network interface 212. During a procedure planning phase, the workstation 136 utilizes computed tomographic (CT) image data or other image data obtained using a different modality, for generating and viewing a three-dimensional model of patient "P's" airways. This process enables the identification of target site "T" (shown in FIG. 5A) to be navigated to in the image data and to coordinate that target with a three-dimensional model (automatically, semi-automatically, or manually). The planning software allows for the selection of a pathway through the patient "P's" airways to target site "T." More specifically, the CT scans are processed and assembled into a three-dimensional CT volume, which is then utilized to generate a three-dimensional model of the patient "P's" airways. The three-dimensional model of the patient "P's" airways may be displayed on a display associated with workstation 136, or in any other suitable fashion. Using the workstation 136, various views of the three-dimensional model of the patient "P's" airways or two-dimensional images generated from the three-dimensional model of the patient "P's" airways may be presented. The three-dimensional model of the patient "P's" airways or the two-dimensional images of the patient "P's" airways may be manipulated to facilitate identification of target site "T." Additionally, the target site may be identified by detecting a biomarker placed at the target site. The biomarker may also be the tool 100. Thereafter, a suitable pathway through patient "P's" airways to access target site "T" can be selected. After a suitable pathway is selected, the pathway is saved and exported to a navigation component of the software for use during the navigation phase(s).

Once the pathway to the target is selected, the EMN system 130 utilizes the EM sensors 102, 120 on the EWC 116 in conjunction with the tracking module 132 to enable tracking and navigation of the EM sensor 102, 120 towards the target site "T." As shown in FIG. 1, the clinician inserts a catheter guide assembly 110, 112 including an EM sensor 102, 120 into a bronchoscope 126 for navigation through a patient "P's" airways. Utilizing the tracking module 132, the location of the EM sensor 102, 120 within the three-dimensional model of the patient "P's" airways can be viewed on the workstation. Using the location of the EM sensor 102, 120 and the three-dimensional model of the patient "P's" airways, the clinician can maneuver and guide the EWC 116 and the tool 100 to the target site "T."

Figure 4:
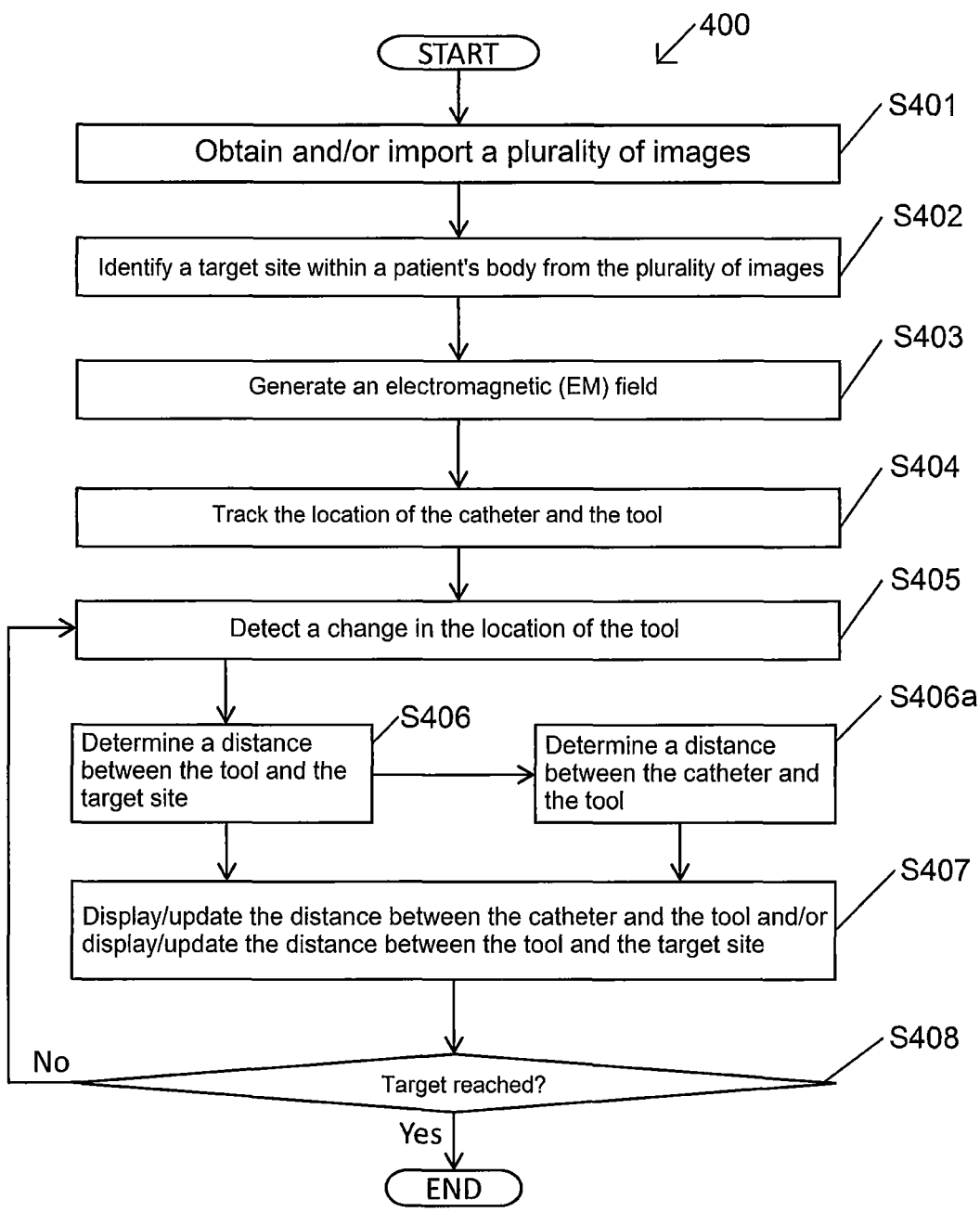
FIG. 4 is a flow diagram of a method for navigating a catheter and a tool to a target site, in accordance with an embodiment of the present disclosure.

With additional reference now to FIG. 4, a flowchart is provided of a computer-implemented method 400 of navigating to a target site "T" and tracking the distance of a tool 100 to a target site "T." The method 400 may be implemented, at least in part, by the processor 202 executing instructions stored in the memory 204 (FIG. 3). Additionally, the particular sequence of steps shown in the method 400 may be executed in sequences other than the sequence shown in FIG. 4 without departing from the scope of the present disclosure. Further, some steps shown in method 400 of FIG. 4 may be concurrently executed with respect to one another instead of sequentially executed with respect to one another.

In an embodiment, the method 400 starts with a plurality of images of a patient being received at S401. For example, the plurality of images may be images of a patient's body that are captured using one or more of a variety of imaging modalities including, but not limited to, computerized tomography (CT) imaging, magnetic resonance imaging (MRI), ultrasound imaging, endoscopic imaging, or fluoroscopic imaging.

At S402, a target site "T" is identified within the patient's body using the images. As described in further detail above, in an embodiment, one or more of the plurality of images obtained in S401 are used by the EMN system 130 to identify and plan a pathway to reach the target site "T."

As shown in FIG. 4, an electromagnetic field generator generates an electromagnetic field around the patient in S403. In this regard, a number of reference sensors 144 placed on the patient "P." The electromagnetic field generator 142 and the reference sensors 144 are interconnected with tracking module 142, which derives the location of each reference sensor 144 in six degrees of freedom. The six degrees of freedom coordinates of reference sensors 144 are sent to workstation 136 where reference sensors 144 are used to calculate a patient coordinate frame of reference.

Figure 5:
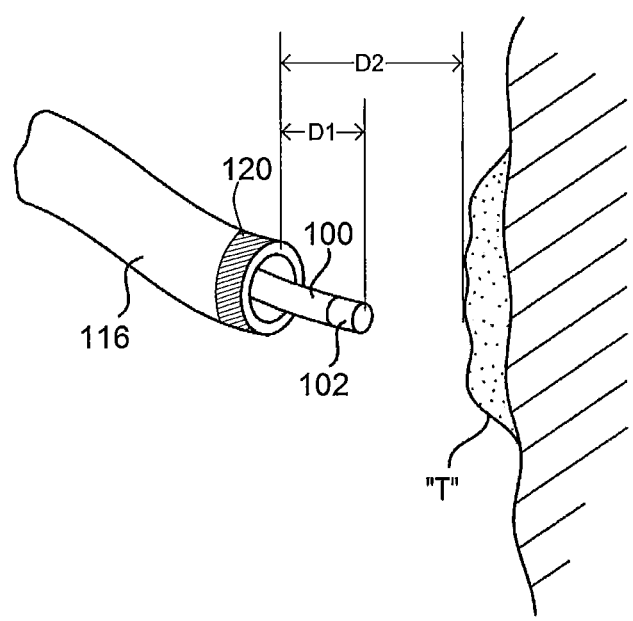
FIG. 5 is a perspective partial-view of a distal portion of an embodiment of a catheter and a tool in a surgical site, in accordance with the present disclosure.

Next, the location of a catheter and/or a tool is tracked at step S404. For example, a catheter, such as EWC 116, is inserted into the patient, where the catheter includes a first EM sensor 120. In an embodiment, the EWC 116 is inserted into a bronchoscope 126. A tool 100 having a second EM sensor 102 is then advanced through the EWC 116. Using the pathway selected during the planning phase, described in detail above, the EWC 116 and tool 102 are navigated towards a target site "T," as shown in FIG. 5. Utilizing the electromagnetic field generator 142 and the reference sensors 144 interconnected with tracking module 142, the EMN system 130 tracks the location of both the EM sensor 120 on the EWC 116 or catheter and the EM sensor 102 on the tool within the patient coordinate frame of reference in S404.

A detection is made as to a change in the location of the tool at step S405. For example, after the EWC 116 and the tool 100 are navigated towards the target site "T," the workstation of EMN system 130 calculates the distance "D1" (shown in FIG. 5) between the distal ends of the EWC 116 and the tool 100 using the EM sensors 102, 120. In an embodiment, the distance "D1" is zero when the distal end of tool 100 is aligned with the distal end of the EWC 116 so that as the tool 100 is advanced past the distal end of the EWC 116, the distance "D1" increases and the change in location of the tool 100 is detected.

A distance is then determined between the tool and a target site, at step S406. For example, workstation 136 calculates the distance between the tool 100 and the target site "T". In an embodiment, since the location of the target site "T" is known based on the acquired CT images and generated planned pathway, the distance "D2" from the EWC 116 and the target site can also be determined. As the tool 100 is advanced past the EWC 116, the distance from the tool 100 to the target site "T" can also be determined.

The determined distance between the EWC 116 and the tool is displayed at step 407. According to an embodiment, the calculated distance "D2" from the EWC 116 and the target site can then be displayed to a user by workstation 136 in real time.

In another embodiment, in addition to the performance of step S406, a distance is calculated between the EWC 116 and the tool 100, at step S406a. As noted above, as a result of the detection of the change of location of the tool 100 in step S405, the distance "D1" may be calculated to indicate the distance the tool 100 is advanced past the EWC 116. Likewise, the calculated distance may be displayed at step S407. For example, the distance "D1" from the EWC 116 and the tool 100 can be displayed to the user. In another embodiment, as shown in FIG. 2C, the EM sensor 102 may be disposed at a location that is closer to a proximal end of the tool 100. In such an embodiment, the EM sensor 102 may not extend outside of the EWC 116. As the tool 100 advances forward, the EM sensor 102 inside the EWC 116 progressively moves toward the EM sensor 120 of the EWC 116, and the distance between the EM sensor 102 inside of the EWC 116 and the EM sensor 120 of the EWC 116 can then be used to determine the distance "D1" between the distal end of the tool 100 and the EM sensor 120.

In S408, a determination is made as to whether the tool 100 has advanced to the target site "T." For example, a determination is made as to whether the distance between the tool 100 and the target site "T" is zero. If the tool 100 has not yet reached the target site "T," the tool 100 is advanced through the EWC 116 or catheter and the method 400 reiterates at S405. As the display is updated at step 407, the display effectively provides a "counting-down" of the distance the tool 100 needs to be advanced before it reaches the target "T." For example, the workstation 136 updates the display to display the updated distance "D2" between the tool 100 and the target site "T." Likewise, the updated distance "D1" between the EWC 116 and tool 100 can be displayed. Returning to step S408, if a determination has been made that the tool 100 has reached the target site "T the process is complete. The tool 100 may then be used to treat the target site "T" and/or it may be removed to allow a different tool to be inserted through the EWC 116 or catheter.

Figure 6:
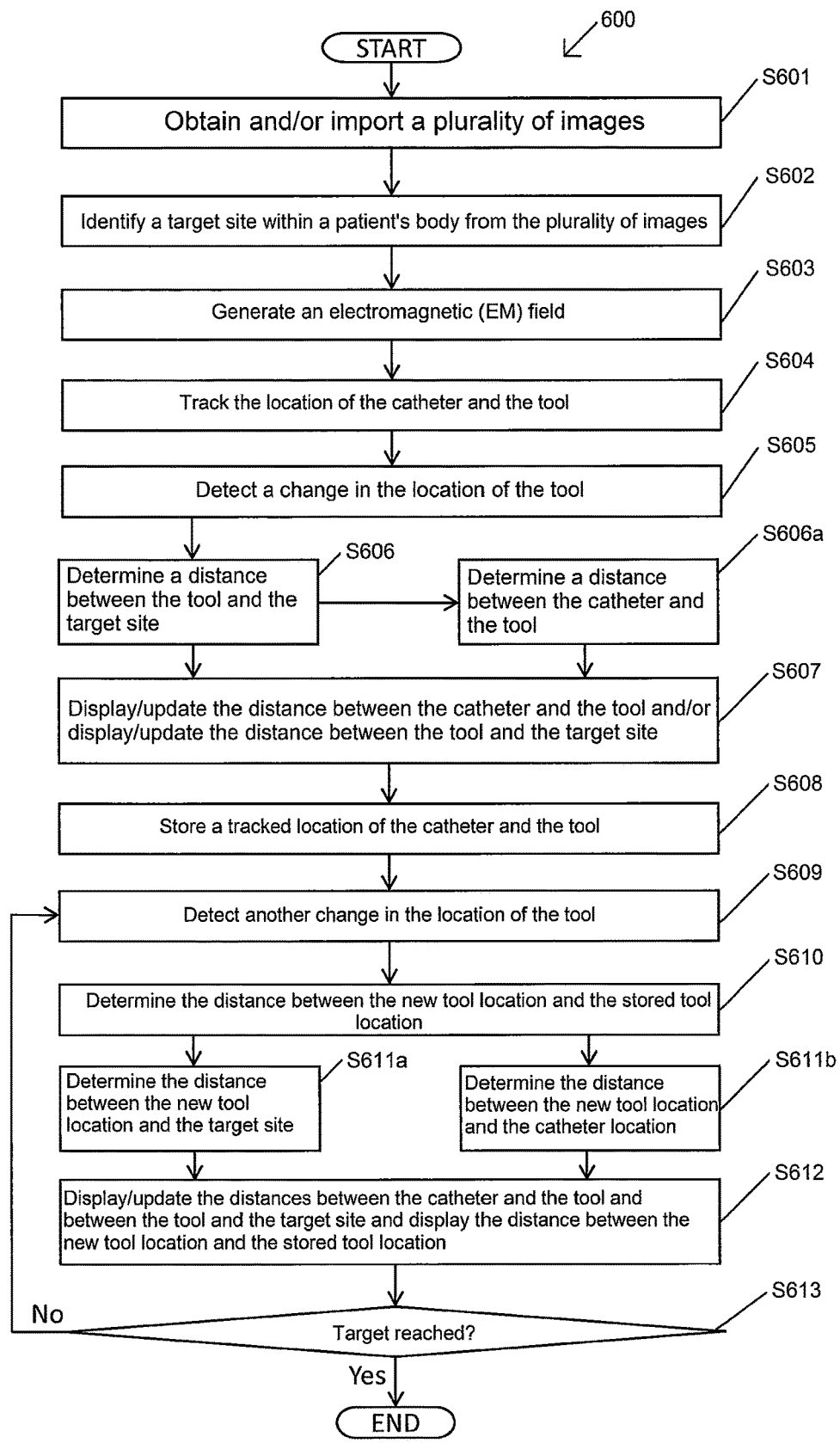
FIG. 6 is a flow diagram of a method for navigating a catheter and a tool to a target site, in accordance with another embodiment of the present disclosure.

With reference now to FIG. 6, a flowchart is provided of a computer-implemented method 600 of navigating to a target site "T" and tracking the distance of a tool 100 to a target site "T," according to another embodiment. The method 600 may be implemented, at least in part, by the processor 202 executing instructions stored in the memory 204 (FIG. 3). Additionally, the particular sequence of steps shown in the method 600 may be executed in sequences other than the sequence shown in FIG. 6 without departing from the scope of the present disclosure. Further, some steps shown in method 600 of FIG. 6 may be concurrently executed with respect to one another instead of sequentially executed with respect to one another. The method 600 of FIG. 6 is described with reference to FIG. 7.

Figure 7:
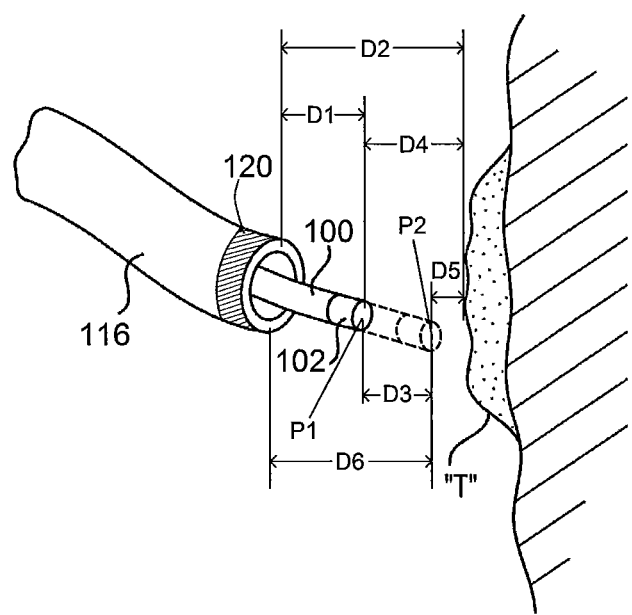
FIG. 7 is a perspective partial-view of a distal portion of an embodiment of a catheter and a tool in a surgical site, in accordance with another embodiment of the present disclosure.

Steps S601 to S604 are performed in a manner substantially similar to steps S401 to S404 of FIG. 4, respectively. At step S605, a detection is made as to a change in the location of the tool. For example, when the distal end of tool 100 is aligned with the distal end of the EWC 116, the distance is zero. However, as the tool 100 is advanced past the distal end of the EWC 116 (or retracted), the distance between the two increases (or decreases) and the change in location of the tool 100 is detected. In an embodiment in which the distal end of the tool 100 is advanced past the distal end of the EWC 116, as shown in FIG. 7, the distal end of the tool 100 may be placed at a location "P1".

A distance is then determined between the tool and a target site, at step S606. For example, workstation 136 calculates the distance between the tool 100 and the target site "T" using the sensor 102 on the distal end of the tool 100. In an embodiment, since the location of the target site "T" is known based on the acquired CT images and generated planned pathway, the distance "D2" from the EWC 116 (for example, via the sensor 120) and the target site "T" can also be determined. In particular, as the tool 100 is advanced past the EWC 116, the distance from the tool 100 to the target site "T" can also be determined (for example, the distance "D4" in FIG. 7).

The determined distance between the EWC 116 and the tool is displayed at step S607. According to an embodiment, the calculated distance "D2" from the EWC 116 and the target site "T" can then be displayed to a user by workstation 136 in real time. Likewise, the distance "D4" between the tool 100 and the target site "T" is displayed to a user by workstation 136 in real time, effectively "counting down" the distance remaining to the target site "T."

In another embodiment, in addition to the performance of step S606, a distance is calculated between the EWC 116 and the tool 100, at step S606a. As a result of the detection of the change of location of the tool 100 in step S605, the distance "D1" may be calculated to indicate the distance the tool 100 has been advanced past the EWC 116. Likewise, the calculated distance may be displayed at step S607. For example, the distance "D1" from the EWC 116 and the tool 100 can be displayed to the user.

In step S608, workstation 136 stores a tracked location of the EWC 116, or catheter, and a tracked location of the tool 100 in memory 204. For example, referring to FIG. 7, the location "P1" at a distal end of the tool 100 when the distance is "D1" may be stored. As the tool 100 is advanced, a change in the location of the tool 100 is detected in step S609, for example, to location "P2". The change in distance "D3" between the new location "P2" of the tool 100 and the stored location "P1" of the tool 100 is then determined in S610. Hence, as the tool 100 is advanced past the distal end of EWC 116, the distance from the tool 100 to the target site "T" also changes. In particular, the change in location of the tool 100 is determined to be "D3." As the distance "D3" increases, the distance "D4" from the distal end of tool 100 to the target site "T" decreases in an equal amount.

The new distance "D5" between the new location "P2" of tool 100 and the target site "T" is then determined in step S611a. Additionally, the distance between the new location of tool 100 and the EWC 116 is also determined in step S611b. The can be determined adding the distance "D3" with distance "D1" to yield the distance "D6". As such, as the distance "D3" increases, the distance from the EWC 116 to the distal end of the tool 100 "D6" increases in an equal amount.

In step S612, the distance between the EWC 116 and the tool 100 "D6" and/or the distance "D5" between the tool 100 and the target site "T" are displayed on workstation 136. Additionally or alternatively, the change in distance "D3" between the new location of tool 100 and the stored location of tool 100 can also be displayed. The displayed distances can be continually updated to present a live "count-down" of the distance remaining from the tool 100 to the target site "T."

In step S613, a determination is made as to whether the tool 100 has advanced to the target site "T." For example, a determination is made as to whether the distance between the tool 100 and the target site "T" is zero. If the tool 100 has not yet reached the target site "T," the tool 100 is advanced through the EWC 116 or catheter and the method 400 reiterates at S609.

Returning to step S613, if a determination has been made that the tool 100 has reached the target site "T the process is complete. The tool 100 may then be used to treat the target site "T" and/or it may be removed to allow a different tool to be inserted through the EWC 116 or catheter.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting but merely as exemplifications of particular embodiments. Those skilled in the art will envision other modifications within the scope and spirit of the claims appended hereto.

What is claimed is:

1. A method for providing tool navigation assistance, comprising:
    determining a distance between a target within a patient's body and a tracked location of a first sensor operably coupled to a catheter using a tracking system;
    displaying the determined distance between the target and the tracked location of the first sensor;
    tracking a location of a second sensor operably coupled to a tool positionable through a lumen of the catheter using the tracking system when the second sensor is in a first position within a patient coordinate frame of reference and when the second sensor is in a second position within the patient coordinate frame of reference
    determining a distance between the tracked location of the first sensor and the tracked location of the second sensor in the first position;
    determining a distance between the tracked location of the second sensor in the first position within the patient coordinate frame of reference and the tracked location of the second sensor in the second position within the patient coordinate frame of reference;
    determining a distance between the tracked location of the first sensor and the tracked location of the second sensor in the second position by adding the determined distance between the tracked location of the first sensor and the tracked location of the second sensor in the first position and the determined distance between the tracked location of the second sensor in the first position and the tracked location of the second sensor in the second position; and
    displaying the determined distance between the tracked location of the first sensor and the tracked location of the second sensor in the second position.

2. The method according to claim 1, further comprising displaying a count-down of a distance remaining between at least one of the first sensor and the target or the second sensor and the target.

3. A method for providing tool navigation assistance, comprising:
    tracking a location of a first sensor operably coupled to a catheter using a tracking system;
    tracking a location of a second sensor operably coupled to a tool positionable through a lumen of the catheter using the tracking system when the second sensor is in a first position within a patient coordinate frame of reference and when the second sensor is in a second position within the patient coordinate frame of reference;
    determining a distance between a target within a patient's body and the tracked location of the first sensor;
    determining a distance between the tracked location of the first sensor and the tracked location of the second sensor in the first position;
    determining a distance between the tracked location of the second sensor in the first position within the patient coordinate frame of reference and the tracked location of the second sensor in the second position within the patient coordinate frame of reference; and
    determining a distance between the tracked location of the first sensor and the tracked location of the second sensor in the second position by adding the determined distance between the tracked location of the first sensor and the tracked location of the second sensor in the first position and the determined distance between the tracked location of the second sensor in the first position and the tracked location of the second sensor in the second position.

4. The method according to claim 3, further comprising:
    obtaining a plurality of images of the patient's body, wherein the plurality of images are computer tomography (CT) images, ultrasound images, magnetic resonance images (MRI), fluoroscopic images, or endoscopic images; and
    identifying the target from the plurality of images.

5. The method according to claim 3, further comprising displaying at least one of the determined distance between the target and the tracked location of the first sensor or the determined distance between the tracked location of the first sensor and the tracked location of the second sensor in the second position.

6. The method according to claim 3, further comprising:
    displaying images of the patient's body; and
    receiving an input on one or more of the images indicating a location of the target.

7. The method according to claim 3, further comprising identifying a location of the target by detecting a biomarker at the target.

8. The method according to claim 3, wherein the first sensor is an electromagnetic sensor and the tracking of the location of the first sensor includes receiving orientation data corresponding to the first sensor using an electromagnetic tracking system.

9. The method according to claim 3, wherein the tool is a needle, a guide wire, a biopsy tool, a dilator, or an ablation device.

10. The method according to claim 3, further comprising:
    displaying the determined distance between the target and the tracked location of the first sensor;
    detecting a change in location of the first sensor;
    determining a distance between the target and the change in location of the first sensor; and
    updating the displayed distance between the target and the tracked location of the first sensor.

11. The method according to claim 3, wherein the catheter includes an extended working channel (EWC), a needle, a guide wire, a biopsy tool, a dilator, or an ablation device.

12. The method according to claim 3, further comprising determining whether the second sensor is advanced to the target by determining whether a distance between the tracked location of the second sensor in the second position and the target is below a preconfigured threshold.

13. The method according to claim 3, further comprising displaying a count-down of a distance remaining between at least one of the first sensor and the target or the second sensor and the target.

14. A navigation system, comprising:
 a catheter configured to be advanced through a patient's luminal network, the catheter having a first sensor and defining a lumen;
 a tool configured to be advanced through the lumen of the catheter, the tool having a second sensor;
 a display configured to display an image of a portion of the patient's luminal network;
 a controller coupled to the display; and
 a memory storing instructions for the controller configured to:
  track a location of the first sensor;
  track a location of the second sensor when the second sensor is in a first position within a patient coordinate frame of reference and when the second sensor is in a second position within the patient coordinate frame of reference;
  determine a distance between a target and the tracked location of the first sensor;
  determine a distance between the tracked location of the first sensor and the tracked location of the second sensor in the first position;
  determine a distance between the tracked location of the second sensor in the first position within the patient coordinate frame of reference and the tracked location of the second sensor in the second position within the patient coordinate frame of reference; and
  determine a distance between the tracked location of the first sensor and the tracked location of the second sensor in the second position by adding the determined distance between the tracked location of the first sensor and the tracked location of the second sensor in the first position and the determined distance between the tracked location of the second sensor in the first position and the tracked location of the second sensor in the second position.

15. The navigation system according to claim 14, wherein the tool is an extended working channel (EWC), a needle, a guide wire, a biopsy tool, a dilator, or an ablation device.

16. The navigation system according to claim 14, wherein at least one of the first sensor or the second sensor is an electromagnetic sensor.

17. The navigation system according to claim 14, wherein the controller is caused to display on the display at least one of the distance between the target and the tracked location of the first sensor or the determined distance between the tracked location of the first sensor and the tracked location of the second sensor in the second position.

18. The navigation system according to claim 14, further comprising an electromagnetic tracking system configured to generate an electromagnetic field for calculating the patient coordinate frame of reference and electromagnetically track the location of the first sensor and the location of the second sensor when the second sensor is in the first position within the patient coordinate frame of reference and when the second sensor is in the second position within the patient coordinate frame of reference.

19. The navigation system according to claim 14, wherein the controller is caused to determine whether a distance between the tracked location of the second sensor in the second position and the target is below a preconfigured threshold.

20. The navigation system according to claim 14, wherein the controller is caused to display on the display a count-down of a distance remaining between at least one of the first sensor and the target or the second sensor and the target.

* * * * *